United States Patent [19]

Terada et al.

[11] 4,419,021

[45] Dec. 6, 1983

[54] MULTI-FUNCTIONAL SENSING OR MEASURING SYSTEM

[75] Inventors: Jiro Terada; Tsuneharu Nitta, both of Katano, Japan

[73] Assignee: Matsushita Electric Industrial Co., Ltd., Osaka, Japan

[21] Appl. No.: 229,185

[22] Filed: Jan. 28, 1981

[30] Foreign Application Priority Data

Feb. 4, 1980 [JP] Japan .................................. 55-12891
May 23, 1980 [JP] Japan .................................. 55-69392

[51] Int. Cl.³ ........................ G01K 7/00; G01W 27/02
[52] U.S. Cl. ..................................... 374/101; 73/336; 73/336.5; 236/46 C; 252/194; 338/25; 338/35; 374/142; 374/164
[58] Field of Search .................... 73/344, 336, 336.5; 361/274, 321; 374/101, 109, 164, 142; 338/25, 35, 23, 24; 236/46 C, 44 C; 219/209

[56] References Cited

U.S. PATENT DOCUMENTS

| | | | |
|---|---|---|---|
| 2,684,592 | 7/1954 | Hadady | 73/336.5 |
| 3,599,862 | 8/1971 | Hogan | 73/336.5 X |
| 3,619,744 | 11/1971 | Stephenson | 361/321 |
| 3,760,244 | 9/1973 | McClelland, Jr. | 361/321 |
| 3,802,268 | 4/1974 | Thoma | 73/336.5 |
| 3,831,450 | 8/1974 | Schipke et al. | 374/109 X |
| 3,906,473 | 9/1975 | LeVine | 340/634 |
| 4,012,692 | 3/1977 | Eicker | 324/715 N |
| 4,067,695 | 1/1977 | Miyaguchi | 338/34 X |
| 4,078,431 | 3/1978 | Motz | 374/109 X |
| 4,086,556 | 4/1978 | Nitta et al. | 338/35 |
| 4,205,364 | 5/1980 | Pereira, Jr. | 361/274 X |
| 4,319,485 | 3/1982 | Terada et al. | 73/344 |

Primary Examiner—Daniel M. Yasich
Attorney, Agent, or Firm—Burgess, Ryan & Wayne

[57] ABSTRACT

A multi-functional sensing and measuring system capable of detecting both temperature and humidity is fabricated from a porous metal-oxide ceramic whose dielectric constant varies with temperature and whose electric resistance varies with ambient humidity. The sensing element is connected in series with a resistor and a rectangular pulse voltage is applied across the series combination, and the ambient temperature and humidity are measured simultaneously in terms of (i) the circuit time constant (to measure temperature) of a transient state value and (ii) the steady state value of the voltage across the resistor (to measure humidity).

6 Claims, 9 Drawing Figures

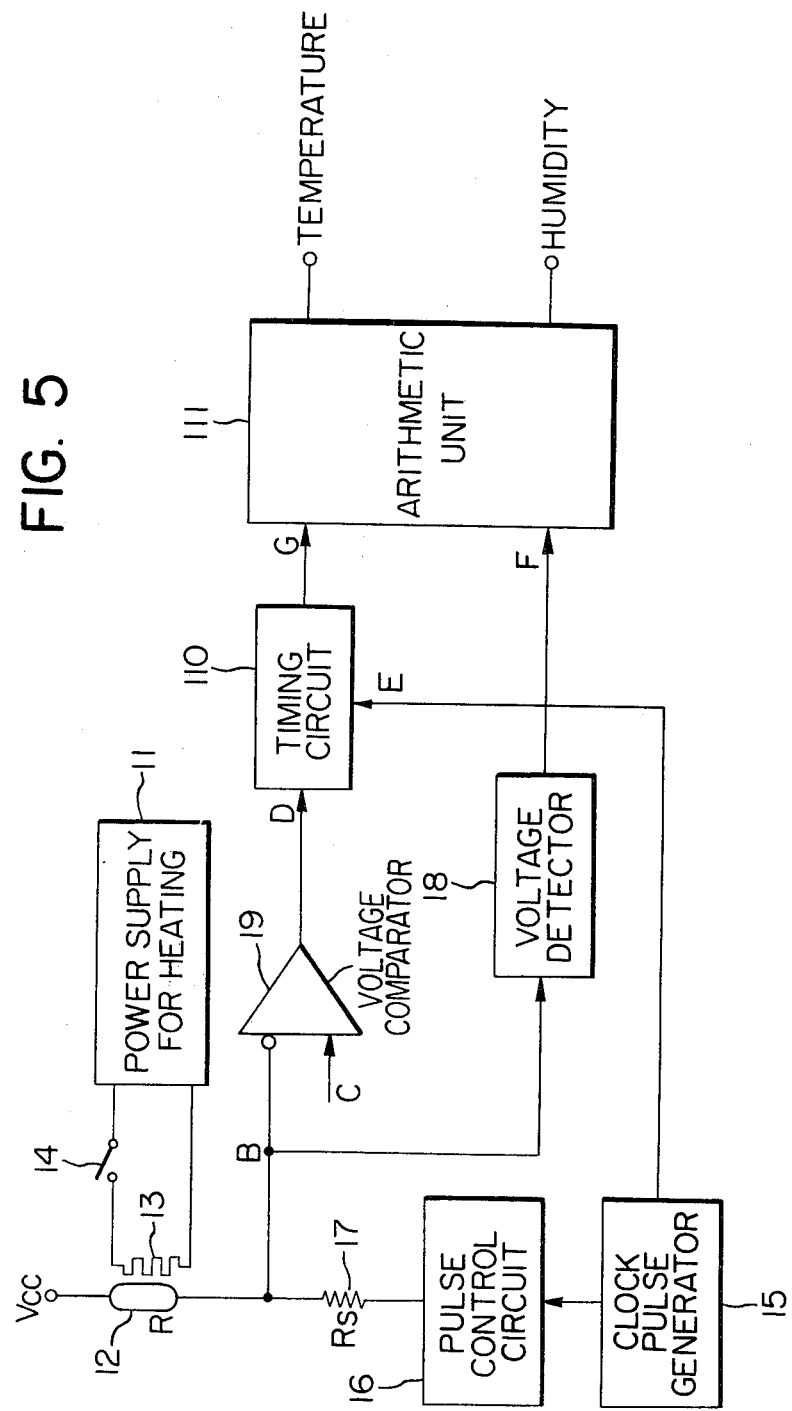

DIVIDED VOLTAGE IN STEADY STATE

MULTI-FUNCTIONAL SENSING OR MEASURING SYSTEM

BACKGROUND OF THE INVENTION

The present invention relates to a multi-functional sensing or measuring system incorporating a multi-functional sensing element both of which are adapted for use in conjunction with air conditioners, driers, cooking equipment and so on for detection of ambient temperature and humidity; that is, a relative humidity.

In general, in order to detect the amount or quantity of water vapor in the surrounding atmosphere, humidity responsive sensing elements have been used and in order to detect temperatures thermocouples and thermistors have been widely used. The humidity responsive sensing elements change their resistance in response to variations in humidity and have been used as a humidity sensor or as a sensor for a humidity control system. As is well known in the art, the humidity responsive sensing elements have been fabricated with metal-oxides such as $Fe_2O_3$, $Al_2O_3$ and so on which have a high water absorption degree. Meanwhile, for one device, equipment or system it would not suffice to detect only an ambient temperature or humidity, and in almost all cases it is required to detect both an ambient temperature and a relative humidity. For instance, the air conditioning system must control both the room temperature and humidity for providing, for instance, comfortable living and working conditions. As a result, a conventional air conditioning system uses a temperature sensing element or elements and a humidity sensing element or elements and includes two control systems responsive to the outputs from these temperature and humidity sensing elements for controlling the temperature and humidity, respectively. Thus the arrangement of these control systems becomes very complex and consequently the costs of air conditioning systems become high.

Recently various industries have been increasingly systematized, so that there has been a strong demand for a single sensing element capable of detecting both an ambient temperature and a relative humidity, but so far there has not devised or proposed a multi-functional sensing element as described above which can detect both an ambient temperature and a relative humidity with a satisfactory degree of accuracy. As a result, the industrial systematization has been much delayed.

The reason why the development of such multifunctional sensing elements of the type described above is difficult is as follows. First, the sensing elements are exposed to the air which contains not only the water vapor but also various components. Some of the components in the air will inevitably cause physical and chemical changes of the sensing elements, and others will adhere to the surfaces of the sensing elements, whereby their temperature and humidity detecting capabilities are degraded. Furtheremore, the relative humidity which is dependent upon the temperature of the air varies over a wide range. Almost all materials respond to variations in relative humidity more or less, but it is extremely difficult to provide a humidity sensing element capable of detecting the relative humidity from 0 to 100%. In general, a conventional humidity sensors have been used for detecting the relative humidity of more than 20% at a temperature less than 80° C. In other words, there has not been devised a multi-functional sensing element capable of detecting a relative humidity from 0 to 100% over a wide temperature variation. Thus without the development of materials which are highly responsive to both temperature and humidity variations, multi-functional sensing elements which are highly reliable, dependable and simple in operation cannot be provided.

Much effort has been made in order to develop sensing elements which are highly reliable in operation and which can vary their electrical characteristics with a high degree of accuracy in response to their absorption water vapor. The recent trend toward such sensing elements is the development of metal-oxide ceramic humidity sensing elements which are thermally stable. However, the degradation of metal oxides due to water vapor absorption is inevitable. Nevertheless, since they are thermally stable, they can be easily regenerated or decontaminated by attaching a heating element to the sensing element or by providing a heating element adjacent to the sensing element so that the latter can be selectively subjected to a heat-treatment.

In general, metal-oxides have a low water absorption capacity; that is, an energy capable of absorbing a small amount of water molecules. As a result, the absorbed water molecules are readily freed from the metal-oxides. This property has been used in humidity sensing elements. More specifically, a humidity sensing element made of metal-oxides exhibits a wide range of resistance change at high humidity due to the absorpotion and desorption of water molecules. Thus the relative humidity can be detected in terms of electrical resistance. However, such humidity sensing elements of the type described have been limited in use to the measurements of dew points and the relative humidity higher than 30%.

Metal-oxide humidity sensing elements have been widely used in the form of an aluminum oxide thin film formed by oxidizing the surfaces of an aluminum thin film, in the form of colloidal particles, in the form of a glaze film consisting of metal oxides and glass or in the form of a ceramic. However, the problem of degradation of their sensitivity due to surface contamination has not yet been solved.

SUMMARY OF THE INVENTION

The present invention was made in order to overcome the above and other problems encountered in the conventional temperature and humidity sensing elements, and has for its object to provide a multi-functional element and a multi-functional sensing or measuring system incorporating this sensing element both of which are highly sensitive to both temperature and humidity variations and can detect, therefore, the ambient temperature and humidity with a high degree of accuracy and which are highly reliable and dependable in operation.

According to the present invention, metal-oxide dielectric ceramics whose dielectric constants are dependent upon ambient temperatures are made porous and consequently a multi-functional sensing element capable of simultaneously detecting both ambient temperatures and relative humidity can be provided. More specifically, a multifunctional sensing element in accordance with the present invention can detect a relative humidity in terms of variations in electrical resistance due to the physical absorption of water vapor in its porous structure. The sensing element also can detect an ambient temperature in terms of variations in its dielectric constant which in turn are converted into variations in electrostatic capacitance or impedance for electric detection.

Another object of the present invention is to provide a novel multi-functional or temperature and relative humidity sensing or measuring system in which a multi-functional sensing element of the type described above and a resistor are connected in series, and a rectangular pulse voltage is applied across this seriesconnected combination so that an ambient temperature and relative humidity can be detected in terms of the value in steady state of a voltage across the resistor (this voltage being referred to as the "divided voltage" in this specification) and a time constant of a transient state value of the divided voltage. More particularly, when the pulse voltage at high frequencies (higher than 1 KHz) is applied to the sensing element, the effect on the dielectric constant of the sensing element due to its water vapor absorption disappears because of a higher degree of dipole moment of water. In other words, in the case of the measurement of temperatures, the effect on the electrostatic capacitance of the sensing element due to the absorption of water vapor into its porous structure disappears. In the multi-functional sensing or measuring system in accordance with the present invention, a pulse voltage is applied across a series combination of a multi-functional sensing element and a resistor. The divided voltage is derived across one of the elements (preferably the resistor) and the steady and transient states, respectively, are measured. The resistance of the multi-functional sensing element (which varies with humidity) is derived from the steady-state divided voltage across the resistor; while the capacitance of the sensing element (which varies with temperature) is measured by monitoring the transient voltage across the resistor and determining its effective rise time, i.e. the time at which said voltage reaches a predetermined threshold value.

The multi-functional sensing or measuring system of the present invention can detect the relative humidity between 1 and 100%; that is, the whole range of relative humidity and a temperature range from -50° to 200° C. The multi-functional sensing element cannot be free from contamination with oil and the like, but it can be completely decontaminated or regenerated when the sensing element is heated above a certain high temperature as described previously. Thus the present invention provides a multi-functional (or temperature and humidity) sensing or measuring system with a single sensing element capable of detecting both the temperature and humidity variations with a high degree of sensitivity and the system will find very valuable applications in various industrial fields.

BRIEF DESCRIPTION OF THE DRAWINGS

FIG. 5 is a block diagram of a multi-functional sensing or measuring system incorporating a multi-functional sensing element in accordance wth the present invention; and FIGS. 6(A)–6(E) show signal waveforms used for the explantion of the mode of operation of the system shown in FIG. 5.

DESCRIPTION OF THE PREFERRED EMBODIMENTS

Figure 1:
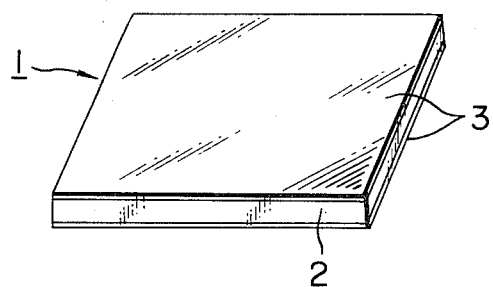
FIG. 1 is a perspective view of a multi-functional sensing element in accordance with the present invention.

In FIG. 1 is shown a multi-functional sensing element in accordance with the present invention. In general, the sensing element 1 comprises a dielectric ceramic substrate 2 and electrodes 3 sintered to the major surfaces of the substrate 2. As will be described in detail below, the substrate 2 is made of a porous metaloxide dielectric.

One example of the fabrication of the dielectric ceramic substrate 2 will be described. 0.5 mol of $BaCO_3$, 1 mol of $TiO_2$ and 0.5 mol of $SrCO_3$ are mixed by a wet process and then dried and finely divided. The finely divided powder is sintered for two hours at 1200° C. and then finely divided again. The powder is formed into pellets or shapes 4 mm × 4 mm × 0.25 mm in size and the pellets or shapes are sintered again at temperatures between 900° C. and 1500° C. Thus ceramic bodies are provided. The steps similar to those described above may be used in preparing ceramic bodies of single metal oxides, spinels, perovskite, tungsten bronze and oxides of alloys such as $MgCr_2O_4$-$TiO_2$.

The sizes of pores and porosity of the dielectric ceramic substrate 2 can be controlled by whether or not a hot pressing process is employed and by sintering conditions such as sintering temperatures. In the case of ceramics, their porosity and sizes of pores can be controlled by changing the sintering conditions as shown in TABLE 1 below.

TABLE 1

| Specimen No. | Sintering Conditions | | | Porosity % | Average sizes of pores micron |
|---|---|---|---|---|---|
| | Sintering temperature °C. | Sintering time hours | Processes | | |
| 1* | 1400 | 2 | hot pressing 350 kg/cm² | 1.5 | 0.1–0.3 |
| 2* | 1400 | 2 | hot pressing 100 kg/cm² | 5.0 | 0.2–0.4 |
| 3 | 1350 | 2 | hot pressing 75 kg/cm² | 10 | 0.3–0.5 |
| 4 | 1350 | 2 | ordinary sintering | 16 | 0.4–0.7 |
| 5 | 1300 | 2 | ordinary sintering | 20 | 0.5–0.8 |
| 6 | 1280 | 2 | ordinary sintering | 22 | 0.7–1.0 |
| 7 | 1250 | 2 | ordinary sintering | 26 | 0.7–1.3 |
| 8 | 1200 | 2 | ordinary sintering | 40 | 3–10 |
| 9* | 1180 | 2 | ordinary sintering | 45 | 4–12 |

*Listed for the sake of comparison.

The electrodes 3 can be formed over the major surfaces of the dielectric ceramic substrate 2 by, for instance, sintering $RuO_2$ paste at 800° C. In addition to $RuO_2$ paste, other pastes of Ag, Ni, Zn, Cr, Pd, Au, Pt, Sn, Cu, Al and In series may be used. It should be noted that the electrodes 3 are porous.

Water absorption degree vs. temperature relationship was investigated with a sample multi-functional sensing element consisting of a substrate 2, for instance, the Sample No. 4 in Table 1, of $Ba_{0.5}Sr_{0.5}TiO_3$ ceramic and $RuO_2$ electrodes 3. The results are shown in FIGS. 2 and 3.

Figure 2:
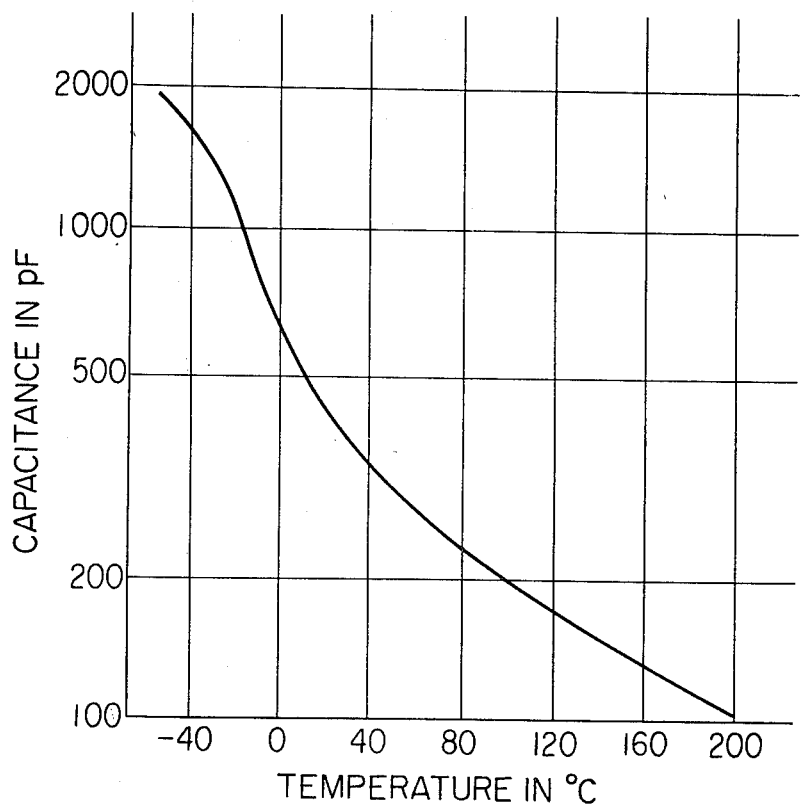
FIG. 2 shows an example of the relationship between the ambient temperature and the bulk electrostatic capacitance of a multi-functional sensing element in accordance with the present invention.

FIG. 2 shows the relationship between the temperature in °C. and the bulk electrostatic capacitance in pF (measured at 1 MHz) of the sensing element. It is evident that the higher the temperature the lower capacitance becomes and that the temperature can be measured in terms of electrostatic capacitance. This temperature-capacitance characteristic will not be adversely affected by the change in relative humidity.

Figure 3:
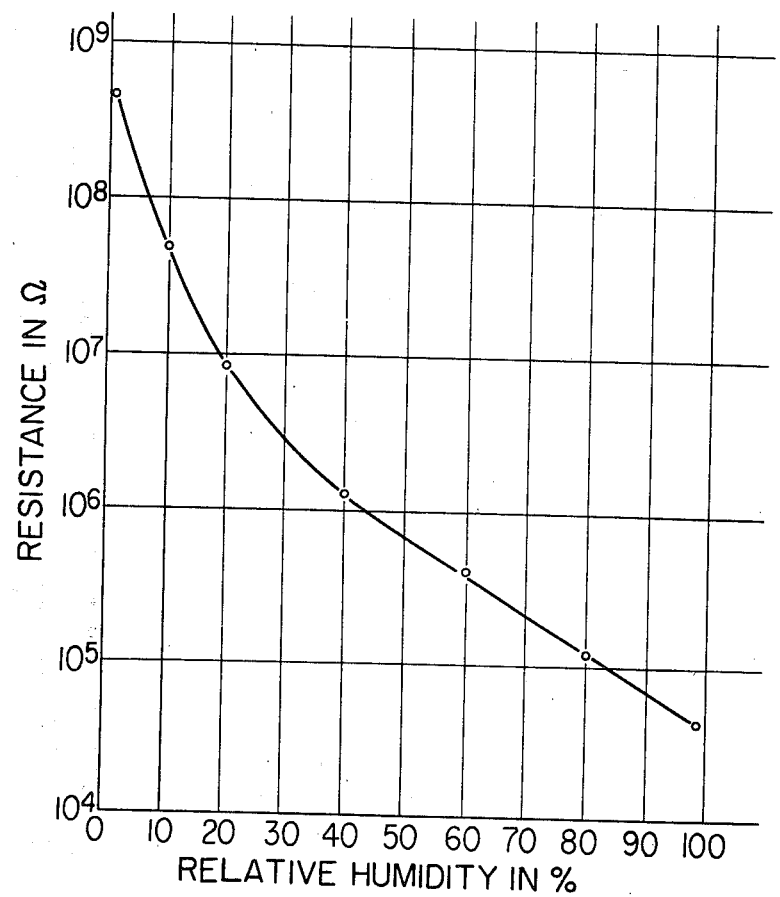
FIG. 3 shows the relationship between the relative humidity and the bulk resistance of the same sensing element.

FIG. 3 shows the relative humidity vs. bulk resistance of the sensing element. It is evident that the higher the relative humidity, the lower the resistance. This relative humidity-resistance characteristic will not be affected by the change in temperature to a noticeable degree.

Thus, it is the characteristics shown in FIGS. 2 and 3 that enable the single sensing element 1 to detect both the temperature and the relative humidity.

Effects on sensitivity of the sensing element 1 of its porosity and sizes of pores were also investigated. The results are as follows. When the average pore size is in excess of 10 microns, the sensitivity of the sensing element drops by 50% in a low temperature range. On the other hand, when porosity is less than 10%, the sensitivity of the sensing element also drops in the low temperature range and when porosity is in excess of 40%, the ceramic sensing element 1 loses its mechanical strength. Thus it is preferable that porosity be between 10% and 40% and that the average pore size be less than 10 microns.

In addition to $Ba_{0.5}Sr_{0.5}TiO_3$ ceramics, investigated were metal-oxide dielectric ceramics containing at least one compound selected from a group consisting of single metal-oxides, spinels, perovskite, tungsten bronze and phrochlore. The results; that is, their characteristics are substantially similar to those described above.

TABLE 2 shows sensitivity to humidity and temperature of various dielectric ceramics provided by making metal-oxide dielectrics porous, these dielectrics having dielectric constants which are dependent upon the temperatures. The specimens shown in TABLE 2 below were so controlled in fabrication that their porosity ranged between 10 and 40% and the sizes of their pores were less than 10 microns.

TABLE 2

| Specimen No. | Component | Temperature response (Ω) RH: 50% (1–95° C.) *(a) | | Humidity response (pF) at 20° C. *(b) | |
|---|---|---|---|---|---|
| | | 20° C. | 150° C. | RH: 20% | RH: 80% |
| 1 | $Pb(Mg_{\frac{1}{2}}W_{\frac{1}{2}})O_3$ | $3.8 \times 10^3$ | $7.0 \times 10^3$ | $2.1 \times 10^7$ | $4.1 \times 10^5$ |
| 2 | $Pb(Cd_{\frac{1}{2}}W_{\frac{1}{2}})O_3$ | $4.0 \times 10^3$ | $1.8 \times 10^3$ | $2.0 \times 10^7$ | $1.5 \times 10^5$ |
| 3 | $Pb(Co_{\frac{1}{2}}W_{\frac{1}{2}})O_3$ | $2.8 \times 10^3$ | $1.5 \times 10^3$ | $2.5 \times 10^7$ | $7.5 \times 10^5$ |
| 4 | $Pb(Sc_{\frac{1}{2}}Nb_{\frac{1}{2}})O_3$ | $5.6 \times 10^2$ | $1.0 \times 10^2$ | $7.0 \times 10^6$ | $5.0 \times 10^4$ |
| 5 | $Pb(Fe_{\frac{1}{2}}Nb_{\frac{1}{2}})O_3$ | $1.8 \times 10^2$ | $2.5 \times 10^1$ | $3.0 \times 10^6$ | $3.4 \times 10^4$ |
| 6 | $Pb(In_{\frac{1}{2}}Nb_{\frac{1}{2}})O_3$ | $9.3 \times 10^2$ | $5.0 \times 10^2$ | $1.6 \times 10^7$ | $5.9 \times 10^4$ |
| 7 | $Pb(Yb_{\frac{1}{2}}Nb_{\frac{1}{2}})O_3$ | $1.5 \times 10^4$ | $4.6 \times 10^3$ | $4.6 \times 10^7$ | $1.0 \times 10^5$ |
| 8 | $Pb(Ho_{\frac{1}{2}}Nb_{\frac{1}{2}})O_3$ | $3.5 \times 10^3$ | $1.8 \times 10^3$ | $3.2 \times 10^7$ | $1.0 \times 10^5$ |
| 9 | $Pb(Fe_{\frac{1}{2}}Ta_{\frac{1}{2}})O_3$ | $1.4 \times 10^2$ | $5.6 \times 10^2$ | $6.0 \times 10^6$ | $5.0 \times 10^4$ |
| 10 | $Pb(Sc_{\frac{1}{2}}Ta_{\frac{1}{2}})O_3$ | $1.8 \times 10^2$ | $5.6 \times 10^2$ | $4.3 \times 10^6$ | $3.0 \times 10^4$ |
| 11 | $Pb(Lu_{\frac{1}{2}}Nb_{\frac{1}{2}})O_3$ | $4.0 \times 10^3$ | $2.2 \times 10^3$ | $2.1 \times 10^7$ | $2.0 \times 10^5$ |
| 12 | $Pb(Lu_{\frac{1}{2}}Ta_{\frac{1}{2}})O_3$ | $4.6 \times 10^3$ | $2.8 \times 10^3$ | $5.2 \times 10^7$ | $2.1 \times 10^5$ |
| 13 | $Pb(Mg_{\frac{1}{3}}Nb_{\frac{2}{3}})O_3$ | $3.0 \times 10^1$ | $2.2 \times 10^2$ | $8.9 \times 10^5$ | $2.2 \times 10^4$ |
| 14 | $Pb(Zn_{\frac{1}{3}}Nb_{\frac{2}{3}})O_3$ | $1.4 \times 10^2$ | $1.4 \times 10^1$ | $1.1 \times 10^6$ | $9.9 \times 10^3$ |
| 15 | $Pb(Co_{\frac{1}{3}}Nb_{\frac{2}{3}})O_3$ | $6.0 \times 10^1$ | $8.0 \times 10^1$ | $1.2 \times 10^6$ | $2.1 \times 10^4$ |
| 16 | $Pb(Ni_{\frac{1}{3}}Nb_{\frac{2}{3}})O_3$ | $4.0 \times 10^2$ | $1.1 \times 10^3$ | $9.5 \times 10^6$ | $2.0 \times 10^5$ |
| 17 | $Pb(Mg_{\frac{1}{3}}Ta_{\frac{2}{3}})O_3$ | $9.3 \times 10^1$ | $1.4 \times 10^3$ | $8.8 \times 10^6$ | $1.1 \times 10^5$ |
| 18 | $Pb(Co_{\frac{1}{3}}Ta_{\frac{2}{3}})O_3$ | $1.4 \times 10^2$ | $9.1 \times 10^1$ | $8.2 \times 10^6$ | $9.1 \times 10^3$ |
| 19 | $Pb(Ni_{\frac{1}{3}}Ta_{\frac{2}{3}})O_3$ | $3.1 \times 10^2$ | $2.0 \times 10^2$ | $9.1 \times 10^6$ | $1.2 \times 10^5$ |
| 20 | $Pb(Fe_{\frac{2}{3}}W_{\frac{1}{3}})O_3$ | $1.4 \times 10^2$ | $5.6 \times 10^2$ | $7.8 \times 10^6$ | $6.8 \times 10^4$ |
| 21 | $Pb(Mn_{\frac{2}{3}}W_{\frac{1}{3}})O_3$ | $1.5 \times 10^2$ | $7.3 \times 10^1$ | $1.4 \times 10^7$ | $2.9 \times 10^4$ |
| 22 | $PbTiO_3$ | $4.2 \times 10^2$ | $3.4 \times 10^2$ | $7.4 \times 10^6$ | $7.6 \times 10^4$ |
| 23 | $KTaO_3$ | $1.05 \times 10^3$ | $*1.75 \times 10^3$ | $1.1 \times 10^7$ | $7.5 \times 10^4$ |
| 24 | $PbHfO_3$ | $2.75 \times 10^3$ | $1.0 \times 10^3$ | $6.3 \times 10^6$ | $8.1 \times 10^4$ |
| 25 | $LiTaO_3$ | $2.8 \times 10^3$ | $2.2 \times 10^3$ | $7.8 \times 10^6$ | $6.2 \times 10^4$ |
| 26 | $LiNbO_3$ | $2.8 \times 10^3$ | $2.1 \times 10^3$ | $7.0 \times 10^6$ | $2.4 \times 10^4$ |
| 27 | $CaTiO_3$ | $1.1 \times 10^3$ | $1.75 \times 10^3$ | $9.0 \times 10^6$ | $7.0 \times 10^4$ |
| 28 | $PbZrO_3$ | $2.9 \times 10^3$ | $1.5 \times 10^3$ | $1.0 \times 10^7$ | $9.0 \times 10^4$ |
| 29 | $NaNbO_3$ | $4.5 \times 10^2$ | $3.2 \times 10^2$ | $7.2 \times 10^6$ | $3.0 \times 10^4$ |
| 30 | $KNbO_3$ | $3.2 \times 10^2$ | $7.0 \times 10^2$ | $9.9 \times 10^6$ | $8.1 \times 10^4$ |
| 31 | $Ba0.5Sr0.5\ TiO_3$ | $1.3 \times 10^2$ | $9.5 \times 10^2$ | $6.5 \times 10^6$ | $1.5 \times 10^4$ |

*Measured at 100° C.
*(a) Measured at 1 MHz.
*(b) Measured at 10 Hz.

Figure 4:
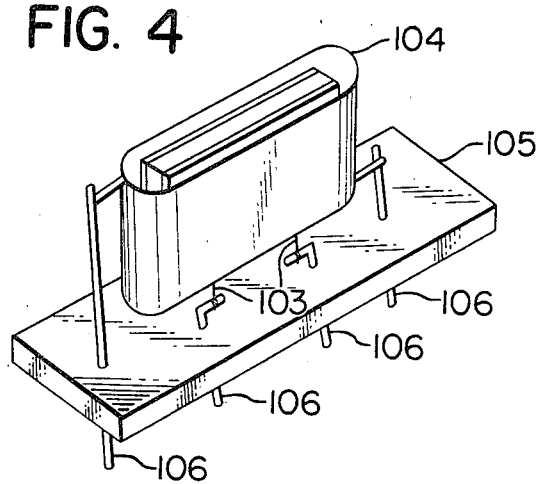
FIG. 4 is a perspective view of a combination of a multi-functional sensing element in accordance with the present invention and a resistance heating element for heating the sensing element.

In FIG. 4 is shown a multi-functional sensor in accordance with the present invention in which a heating element 104 is provided to heat a sensing element 1 with lead wires 103 to temperatures between 250° C. and 1000° C. The sensing element 1 and the heating element 104 are mounted on a base 105 with connection terminals 106. In addition to the heating element arrangement shown in FIG. 4 (which may be called the indirect type), a direct heating arrangement may be also employed. In the latter case, one of the electrodes 3 of the heating element 2 also serves as a heating element for directly heating the element 2.

In FIG. 5 is shown in block diagram a metering system incorporating a multi-functional sensor in accordance with the present invention. When a switch 14 is closed, current flows from a power supply 11 into a heating element 13 so as to raise the temperature of a sensing element 12 to a desired level as described previously and to effect the heat-cleaning. A clock pulse generator 15 generates and delivers clock pulses to a pulse control circuit 16 and a timing circuit 110. The pulse control circuit 16 receives the clock pulses from the clock pulse generator 15 and processes them in such a way that they may have a predetermined pulse width or duration and a predetermined pulse duty factor. The output voltage pulses from the pulse control circuit 16 are delivered to the sensing element 12 through a resistor 17 which has a function of detecting the level of current flowing into the sensing element 12. A voltage detector 18 is adapted to detect a voltage divided by the sensing element 12 and the resistor 17. A voltage comparator 19 compares the voltage divided by the sensing element 12 and the resistor 17 with a reference voltage and generates an output signal representative of the difference between the two voltages. The output from the comparator 19 is delivered to the timing circuit 110 which in turn detects the time duration of the output from the comparator 19; that is, a time constant of a transient state value of the divided voltage. The output from the voltage detector 18 and the output from the timing circuit 110 are applied to an arithmetic unit 111 which in turn not only converts the output from the timing circuit 110 into an analog or digital signal representative of the measured temperature but also converts the output from the voltage detector 18 into an analog or digital signal representing the detected humidity. In addition, the arithmetic unit 111 displays the measured temperature and humidity. Furthermore, the unit 111 can effect self-compensations such as temperature and humidity compensations in response to the detected temperature and humidity.

Figure 6A:
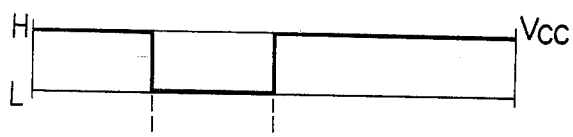
Figure 6B:
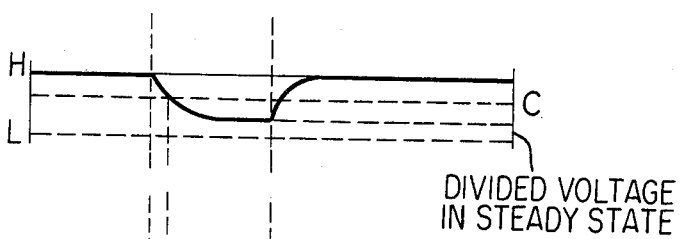

The mode of operation of the metering system shown in FIG. 5 will be described in more detail with further reference to FIGS. 6(A)–6(E). First a pulse voltage from the pulse control circuit 16 as indicated in FIG. 6(A) is applied across a series-connected circuit consisting of the sensing element and the resistor 17 and a divided voltage and a time constant are detected. The pulse voltage rises to a high level H and drops to a low level L. The voltage B, shown in FIG. 6(B), derived by the division of $V_{cc}$ by the sensing element 12 and the resistor 17 is expressed by $$B = \frac{R_s}{R + R_s} V_{cc} \tag{1}$$

where R is the resistance of the sensing element 12, and $R_s$ is the resistance across the resistor 17. The divided voltage B refers to the "steady state voltage" as indicated in FIG. 6(B) after the pulse voltage A has been applied. In order to detect the humidity with a maximum degree of sensitivity, a resistor 17 having a value equal to that of the sensing element 12 at a given humidity is inserted in series with the element 12. For instance, the value of the resistor 17 is 800 kΩ at the relative humidity of 50%.

A time constant of a transient divided voltage is derived from the electrostatic capacitance and resistance of the sensing element 12 and the value $R_s$ of the resistor 17. As described previously, the electrostatic capacitance of the sensing element 12 changes in response to variations in temperature (See FIG. 2) and subsequently the time constant changes in response to the variations in temperature of the sensing element 12.

Figure 6D:
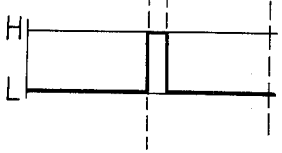
Figure 6E:

The voltage comparator 19 compares a potential at the point B with the reference voltage C. Then a pulse with a pulse duration or width corresponding to the time constant appears at a point D as shown in FIG. 6(D). The duration or width of the pulse D is measured by the timing circuit 110. The pulse D is drawn into the timing circuit 110 within the duration of the signal E (See FIG. 6E) from the clock pulse generator 15. The output G from the timing circuit 110 represents the temperature.

To detect the humidity, the steady-state value of the divided voltage B across resistor 17 of the voltage divider comprising sensing element 12 and resistor 17 is converted into the output voltage F by the voltage detector 18. Thus the resistance and capacitance of the sensing element 12 can be obtained from the divided voltage B and the time constant G respectively; and the humidity and temperature to which the sensing element 12 is subjected can be obtained from the detected resistance and capacitance of the sensing element 12 respectively.

Since the resistance of the sensing element 12 changes in response to the variation in humidity, the transient time constant (which is affected by both the resistance and the capacitance of the sensing element 12) changes in response to changes in humidity as well as changes in temperature. Nevertheless, the temperature and humidity can be detected independently of each other, since the resistance of the sensing element 12 is determined by the steady-state value of the divided voltage B (which is independent of the sensing element capacitance) and this resistance value, together with the time constant G, can be used to calculate the sensing element capacitance.

The output E from the voltage detector 18 and the output G from the timing circuit 110 may be coupled to suitable display devices or temperature and humidity control systems. In addition, when the arithmetic unit 111 receives the outputs F and G and carries out the temperature and humidity compensations as described previously; the humidity-compensated temperature detection and the temperature-compensated humidity detection can be made with a higher degree of accuracy.

As described previously, the arithmetic unit 111 is further adapted to convert the outputs F and G into suitable analog or digital signals for displays.

The characteristics similar to those of the $Ba_{1-x}Sr_xTiO_3$ (where $x = 0 \sim 1$) described previously were also obtained when the sensing elements were in the form of a ceramic body or film of at least one metal-oxide selected from a group consisting of perovskite, spinels, pyrochlore, steatite and single metal oxides. They are, for example, $MgTiO_3$, $CaTiO_3$, $KTaO_3$, $PbHfO_3$, $LiTaO_3$, $LiNbO_3$, $BaZrO_3$, $CaZrO_3$, $SrZrO_3$, $MgZrO_3$, $PbZrO_3$, $NaNbO_3$, $KNbO_3$, $PtTiO_3$ and so on.

The measuring system of the type shown in FIG. 5 can be controlled in a digital or analog manner.

What is claimed is:

1. A multi-functional sensing system capable of detecting both the temperature and humidity to which it is subjected, comprising:
   (a) a sensing element comprising a porous dielectric metal oxide ceramic plate the dielectric constant of which varies with temperature and the electric resistance of which varies with humidity, the major surfaces of said ceramic plate having a pair of electrodes thereon, (b) a resistor element connected in series with said sensing element to one of the electrodes of said pair of electrodes on one of the major surfaces, (c) a rectangular pulse generator means for supplying rectangular pulses across said sensing element and resistor element, (d) means in an electrical circuit connected to the junction of the sensing element and the resistor element for determining temperature by detecting the time difference between the time at which the pulse signal is applied and the time required for the voltage across one of said elements of said series connected elements to reach a reference voltage level, and (e) means in the electrical circuit connected to the junction of the sensing element and the resistor element for detecting humidity by determining the amplitude of the steady state voltage across one of said elements of said series connected elements.

2. A multi-functional sensing system as set forth in claim 1, wherein the size of pores of said dielectric ceramic is less than 10 microns.

3. A multi-functional sensing system as set forth in claim 1, wherein the porosity of said dielectric ceramic plate is between 10% and 40%.

4. A multi-functional sensing system as set forth in claim 1, 2 or 3, wherein said dielectric ceramic comprises a metal-oxide material selected from the group consisting of perovskite structures or systems, pyrochlore structures or systems, spinel structures or systems, steatites and single metal oxides of $Ba_{1-x}Sr_xTiO_3$, (where $x=0\sim1$), $MgTiO_3$, $CaTiO_3$, $KTaO_3$, $PbHfO_3$, $LiTaO_3$, $LiNbO_3$, $BaZrO_3$, $CaZrO_3$, $SrZrO_3$, $MgZrO_3$, $PbZrO_3$, $NaNbO_3$, $KnbO_3$ and $PbTiO_3$.

5. A multi-functional sensing system as set forth in claim 1 wherein said sensing element includes a resistance heating element.

6. A multi-functional sensing system capable of measuring both the temperature and humidity to which it is subjected, comprising:

a sensing element comprising a porous dielectric metal oxide ceramic plate, the dielectric constant of which varies with temperature and the electric resistance of which varies with humidity, the major surfaces of said plate each having at least one electrode thereon;

a pulse generating circuit;

a resistor element connected in series with said sensing element to said pulse generating circuit; voltage comparator means having an input connected across at least one of said elements for generating an output threshold signal;

a timing circuit coupled to said voltage comparator means and said pulse generating circuit for providing a time signal corresponding to the interval between the time at which a pulse is generated by said pulse generating circuit and the time at which said output threshold signal of said voltage comparator means is generated;

a steady state voltage detector for generating a voltage signal corresponding to the amplitude of the steady state potential at said one of said electrodes; and data processing means (i) responsive to said time signal for providing a first output indicative of the temperature to which said sensing element is subjected and (ii) responsive to said voltage signal for providing a second output indicative of the humidity to which said sensing element is subjected.

* * * * *